US007956003B2

(12) United States Patent
Revault et al.

(10) Patent No.: US 7,956,003 B2
(45) Date of Patent: Jun. 7, 2011

(54) CATALYST COMPONENTS BASED ON FERRICINIUM COMPLEXES USED FOR OLEFIN POLYMERISATION

(75) Inventors: Cyril Revault, Sainte Adresse (FR); Olivier Lavastre, Gahard (FR); Sabine Sirol, Horrues (BE)

(73) Assignees: Total Petrochemicals Research Feluy, Seneffe (Feluy) (BE); Centre National de la Recherche Scientifiqaue (CNRS), Paris (FR)

( * ) Notice: Subject to any disclaimer, the term of this patent is extended or adjusted under 35 U.S.C. 154(b) by 0 days.

(21) Appl. No.: 12/295,473

(22) PCT Filed: Mar. 27, 2007

(86) PCT No.: PCT/EP2007/052910
§ 371 (c)(1),
(2), (4) Date: Oct. 6, 2009

(87) PCT Pub. No.: WO2007/113169
PCT Pub. Date: Oct. 11, 2007

(65) Prior Publication Data
US 2010/0063230 A1 Mar. 11, 2010

(30) Foreign Application Priority Data
Mar. 30, 2006 (EP) .................................. 06290538

(51) Int. Cl.
*B01J 31/22* (2006.01)
*C07C 2/32* (2006.01)
*C07C 2/34* (2006.01)
(52) U.S. Cl. ........ 502/155; 502/103; 502/113; 502/152; 502/167; 585/520; 585/527
(58) Field of Classification Search ................. 502/103, 502/113, 152, 155, 167; 585/520, 527
See application file for complete search history.

(56) References Cited

OTHER PUBLICATIONS

Bernardi, Luca, et al., "Diastereoselective Additions of Organometallic Reagents to (SFC)-2-p-Tolylsulfanylferrocene Carboxyaldehyde and to (SFC)-2-p-tolyisulfanyl Ferrocenyl Imines. Synthesis of New Central and Planar Chiral Ferrocenyl Alcohols and Amines," Arkivoc (ii), 2004, pp. 72-90.
Bonini, Bianca F., et al., "One Pot Synthesis of New B-Lactams Containing the Ferrocene Moiety," Synlett No. 7, 2001, pp. 1092-1096.
Bosque, Ramon, et al., "Heterodi- and Heterotrimetallic Compounds Containing Five-Membered Rings and o(Pd-Csp2, ferrocene) Bonds. X-ray Crystal Structure of the Meso-Form of [Pd2(Fe(n5-C5H3)-C(CH3)=N-C6H5)}2Cl2(PPh3)2]," Organometallics, vol. 18, No. 7, 1999, pp. 1267-1274.
Bosque, Ramon, et al., "Influences of the Substituents at the Iminic Carbon Atoms (Hydrogen versus Methyl) Upon the Properties of Ferrocenylimines and their Cyclopalladated Derivatives+," Journal of Chemical Society, Dalton Transactions, 1994, pp. 735-745.
Bosque, Ramon, et al., "Substituent Effects on the Electrochemical Behavior of Iron (II) in Schiff Bases Derived from Ferrocene and their Cyclopalladated Compounds," Inorganica Chimica Acta 244, 1996, pp. 141-145.
Bullita, E., et al., "Synthesis, X-ray Structural Determination and Mossbauer Characterization of Schiff Bases Bearing Ferrocene Groups, Their Reduced Analogues and Related Complexes," Inorganica Chimica Acta 287, 1999, pp. 117-133.
Cui, Xiuling, et al., "Bis[1,1'-N,N'-(2-picolyl)aminomethyl]ferrocene as a Redox Sensor for Transition Metal Ions," Dalton Transactions, No. 11, 2004, pp. 1743-1751.
Gibson, Vernon C., et al., "Ferrocene-Substituted Bis(Imino)Pyridine Iron and Cobalt Complexes: Toward Redox-Active Catalysts for the Polymerization of Ethylene," vol. 25, No. 8, 2006, pp. 1932-1939.
Gibson, Vernon C., et al., "Synthetic, Spectroscopic and Olefin Oligomerisation Studies on Nickel and Palladium Complexes Containing Ferrocene Substituted Nitrogen Donor Ligands," Dalton Transactions, No. 5, 2003, pp. 918-926.
Lewkowski, Jaroslaw, et al., "a-(Ferrocenyl)-aminomethanephosphonous Acids. First Synthesis and Preparation of Their Esters with Cholesterol and Adenosine," Journal of Organometallic Chemistry 689, 2004, pp. 1684-1690.
Lewkowski, Jaroslaw, et al., "First Synthesis of 1,1'-ferrocene Bisaminophosphonic Esters," Journal of Organometallic Chemistry 689, 2004, pp. 1265-1270.
Lewkowski, Jaroslaw, et al., "The First Synthesis of Ferroceynl Aminophosphonic Esters," Journal of Organometallic Chemistry 631, 2001, pp. 105-109.
Lopez, Concepcion, et al., "Cyclopalladated Compounds Derived From Ferrocenylimines. Crystal Structure of [Pd{(n5-C5H5)Fe[n5-C5H3CH=N(CH2)2Ph]}Cl(PEt3)]+," Journal of Chemical Society, Dalton Transactions, Issue 1, 1992, pp. 2321-2328.
Lopez, Concepcion, et al., "Effects of the Nature of the Nitrogen Donor Atom (sp2 versus sp3) Upon the Properties and Chemistry of Palladated Complexes with a(Pd-Csp2, Ferrocene) Bonds+," Journal of Chemical Society, Dalton Transactions, 1994, pp. 3039-3046.
Lopez, Concepcion, et al., "Relationships Between 57Fe NMR, Mossbauer Parameters, Electrochemical Properties and the Structures of Ferrocenylketimines," Journal of Organometallic Chemistry 691 (2006) 475-484.
Peet, J.H.J., et al., "Novel Photoreaction Products of N-Substituted Ferroceneylimines," Journal of Organometallic Chemistry 88, 1975, pp. C1-C3.
Perez, Sonia, et al., "Trans-influences in Mononuclear Cyclopalladated Compounds Containing a a(Pd-Csp2, ferrocene) Bond. X-ray Crystal Structures of [Pd{(n5-C5H3)-CH=N-CH2-C6H5]Fe(n5-C5H5)}(X)(PPh3)] with X-=Br- and I-," Journal of Organometallic Chemistry 625, 2001, pp. 67-76.
Revault, Cyril, et al., U.S. Appl. No. 12/295,464, filed Sep. 30, 2009, "Catalyst Components Based on Ferrocenyl Complexes Used for Olefin Polymerisation,".
Walther, Dirk, "Furfurylidene-imines as Components of the Oxidative Coupling with CO2 at Nickl(0) Centers; Influence of the Subtituents on the Structure of the Resulting Nickelacycles," Zeitschrift Fuer Anorganische Und Allgemeine Chemie, vol. 628, No. 4, 2002, pp. 851-862.
Zhao, Gang, et al., "Cyclic Ether Induced Assymetric Cyclopalladation: Synthesis and Structural Characterization of Enantiopure Bis(u-acetato)-Bridged Dimers of Planar Chiral Cyclopalladated Ferrocenylimines and Their Derivatives," Organometallics No. 18, 1999, pp. 3623-3636.

*Primary Examiner* — Caixia Lu

(57) ABSTRACT

The present invention discloses catalyst components based on ferricinium ligands, their method of preparation and their use in the polymerisation of olefins.

7 Claims, No Drawings

CATALYST COMPONENTS BASED ON FERRICINIUM COMPLEXES USED FOR OLEFIN POLYMERISATION

The present invention discloses catalyst components based on ferricinium ligands, their method of preparation and their use in the polymerisation of olefins.

In the search for new catalyst components capable of producing highly tunable polymers, some ferrocene complexes have been known to polymerise or co-polymerise ethylene such as for example the ferrocene-substituted bis(imino) pirydine iron and cobalt complexes disclosed by Gibson et al. in Gibson V. C., Long N. J., Oxford, P. J., White A. J. P., and Williams D. J., in Organometallics (ASAP article DOI 10.1021/om0509589), or for example the ferrocene-substituted bis(imino) nickel and palladium complexes disclosed by Gibson et al. in J. Chem. Soc. Dalton Trans. 2003, 918-926.

They carried out an oxidation of the metallic complex resulting from the metallation of the ferrocene complex. This complex was used in the polymerisation of ethylene and showed the same level of activity as the non-oxidised equivalent metallic complex.

There is a need to develop new catalyst system having good activity and able to produce polymers tailored to specific needs.

It is an aim of the present invention to prepare new catalyst components that can be used in the polymerisation of olefins.

It is also an aim of the present invention to provide very active catalyst components.

It is another aim of the present invention to provide a method for polymerising or copolymerising olefins.

The present invention reaches, at least partially, any one of those aims.

Accordingly, the present invention discloses a ferricinium ligand of formula

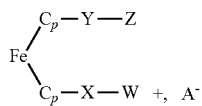

wherein Cp is a cyclopentadienyl group, unsubstituted or substituted, with chelating arms,
wherein X and Y are the same or different with the restriction that at least one Y or X contains at least one chelating group in direct connection with the ferricinium, the other of Y or X being optionally present,
wherein Z and W are each independently selected from alkyl, aryl, heterocycle group or non-heterocycle group containing ether, thioether, phosphine, imine, amine or amide,
wherein iron has been oxidated with an oxidant capable to oxidate $Fe^{II}$ into $Fe^{III}$ but mild enough to preserve the ligand, and
wherein $A^-$ is an anion associated to $Fe^{III}$.

The ligands of the present invention satisfy two conditions:
The oxidation reaction of ferrocene into ferricinium is reversible.
The oxidation reaction does not destroy the ligand.
The oxidised ligand can react with metal precursors to produce corresponding complexes.

In a preferred embodiment according to the present invention, X and/or Y are each independently selected to include atoms O, N, P, S or groups —CR=CR—, —CR=N—, —N=CR— or —C≡C— wherein R is H, alkyl or aryl groups having at most 20 carbon atoms. The link between Y and Z and/or X and W can present a conjugation or not.

More preferably, the groups Y—Z and/or X—W are each independently selected from CH=N—CH2-Ar wherein Ar is phenyl, furyl or pyridine group.

Most preferably there is only one substituent group Y—Z or X—W, the other being hydrogen.

The most preferred complex according to the present invention is

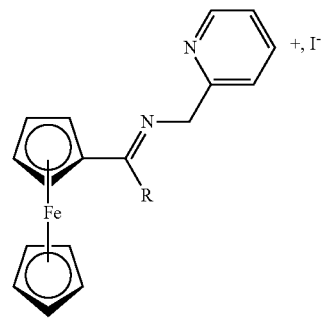

The oxidation reaction can be carried out chemically or electrochemically.

In a preferred embodiment according to the present invention, it is carried out chemically with a mild oxidant. The oxidant is selected in order to have a potential from 550 to 900 mV versus calomel reference. Among the most preferred oxidants, one can cite iodine. It has a potential of about 600 mV and thus does not destroy the ligand. In addition, the reduced form of the oxidant and the oxidant itself are easily separated and removed from the oxidised ligand.

The oxidised ligand is isolated before complexation with the metal.

The present invention also discloses a method for preparing the oxidized ligand that comprises the steps of:
a) dissolving the ferrocene ligand into a solvent;
b) adding iodine to the solution;
c) stirring the mixture at a temperature of from 20 to 80° C. and during a period of time of from a few minutes to 12 hours;
d) evaporating the solvent;
e) washing with appropriate solvent to separate the reduced form of the oxidant and/or excess of the oxidant itself from the oxidised ligand.
f) retrieving the oxidised ligand.

Preferably the oxidation reaction is carried out at room temperature overnight.

The preferred solvent is polar and dissolves all reaction products, more preferably, it is acetonitrile (MeCN).

The following scheme can for example be used.

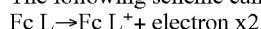
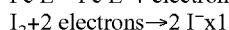
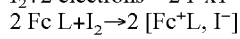

The ligand is then complexed with the metal by complexation reaction with a metallic precursor $M(Hal)_n R'_{v-n}$ in a solvent, wherein M is a metal Group 6 to 10 of the Periodic Table, each Hal is the same or different and is halogen, each R' is the same or different and is substituted or unsubstituted hydrocarbyl having from 1 to 20 carbon atoms, substituted or unsubstituted aryloxy or alkoxy, v is the valence of M and n is zero or an integer at most equal to v.

Preferably M is Ni, Co, Fe, Pd or Cr.
Preferably Hal is chlorine.
Preferably n is equal to v.

The solvent may be selected from dichloromethane or tetrahydrofuran and the complexation reaction is carried out at room temperature or at reflux.

Typically, two types of metallic complexes could be formed, one where the metal is coordinated to one ligand and one where the metal is coordinated to two ligands. The relative amounts of each ligand and metal unit depend upon the nature of ligand and of the metal. The amount of ligand must therefore be of at least one equivalent of ligand per metallic equivalent.

The present invention further discloses an active catalyst system comprising the metallic complex and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

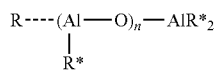

for oligomeric, linear aluminoxanes and by formula

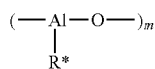

for oligomeric, cyclic aluminoxane,
wherein n is 1-40, preferably 10-20, m is 3-40, preferably 3-20 and R* is a $C_1$-$C_8$ alkyl group and preferably methyl.

The amount of activating is selected to give an Al/M ratio of from 100 to 3000, preferably of about 1000.

Suitable boron-containing activating agents may comprise a triphenylcarbenium boronate such as tetrakis-pentafluorophenyl-borato-triphenylcarbenium as described in EP-A-0427696, or those of the general formula $[L'-H]+[B\ Ar_1\ Ar_2\ X_3\ X_4]-$ as described in EP-A-0277004 (page 6, line 30 to page 7, line 7). The amount of boron-containing activating agent is selected to give B/M ratio of from 0.5 to 5, preferably of about 1.

In another embodiment, according to the present invention, the metallic complex may be deposited on a conventional support impregnated with an activating agent. Preferably, the conventional support is silica impregnated with methylaluminoxane (MAO). Alternatively, it can be an activating support such as fluorinated alumina silica.

The present invention further discloses a method for preparing an active catalyst system that comprises the steps of:
a) providing an oxidized ferricinium ligand;
b) complexing the ligand of step a) with a metallic salt $M(Hal)_n R'_{v-n}$ in a solvent;
c) retrieving a catalyst component;
d) activating the catalyst component with an activating agent having an ionising action;
e) optionally adding a cocatalyst;
f) retrieving an active oligomerisation or polymerisation catalyst system.

Alternatively, in step d), the catalyst component is deposited on a support impregnated with an activating agent.

The cocatalyst may be selected from triethylaluminium, triisobutylaluminum, tris-n-octylaluminium, tetraisobutyl-dialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor;
b) injecting the monomer and optional comonomer;
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

The present invention also discloses the polymers obtained with the new catalyst systems.

EXAMPLES

All reactions were performed using standard Schlenk techniques or in an argon-filled glove-box. The starting materials and reagents, purchased from commercial suppliers, were degassed and purified by distillation under nitrogen using standard drying agents.

Preparation of Ligands.

Synthesis of N-ferrocenylidenebenzylamine (F1)

All complexes were prepared according to the method described for example in Gibson et al. (Chem Soc Rev., 2004, 33, 313-328) or in Samuelson et al. (Journal of Organometallic Chemistry, 1999, 575, 108-118).

300 mg (1.4 mmol) of solid ferrocenecarboxaldehyde were introduced in a schlenk. 90 µL (2.1 mmol) of benzylamine and 2 mg of p-toluene sulfonic acid were added. The mixture was dissolved in 20 mL of toluene and the homogeneous mixture was stirred and heated at reflux overnight (16 h). The solution was cooled down to room temperature (25° C.) and the solvent was vaporised under vacuum. After drying overnight under vacuum and at a temperature of 50° C., 374.7 mg (1.28 mmol) of orange solid were obtained with a yield of 91%.

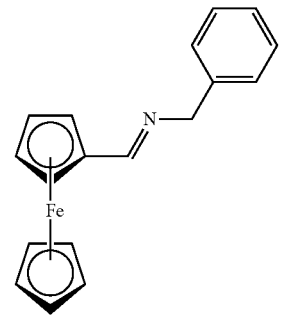

RMN$^1$H (200 MHz, CDCl$_3$): δ 8.26(s, CH=N, 1H); 7.4-7.3 (m, ArH, 5H); 4.73 (m, C$_5$H$_4$, 2H); 4.69 (s, CH$_2$Ph, 2H); 4.31 (m, C$_5$H$_4$, 2H); 4.20 (s, C$_5$H$_5$, 5H)

Synthesis of N-ferrocenylidenefurfurylamine (F2)

300 mg (1.4 mmol) of solid ferrocenecarboxaldehyde were introduced in a schlenk. 138 µl (2.1 mmol) of furylamine and 2 mg of p-toluene sulfonic acid were added. The mixture was dissolved in 20 mL of toluene and the homogeneous mixture was stirred and heated at reflux overnight (16 h). The solution was cooled down to room temperature and the solvent was vaporised under vacuum. After drying overnight under vacuum and at a temperature of 50° C., 381 mg (1.30 mmol) of orange solid were obtained with a yield of 93%.

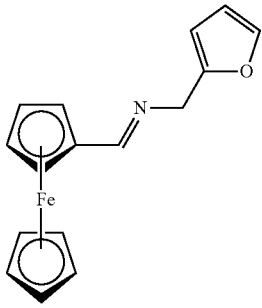

RMN$^1$H (200 MHz, CDCl$_3$): δ 8.20 (s, CH=N, 1H); 7.39 (m, H$_{fur}$, 1H); 6.35 (m, H$_{fur}$, 1H); 6.26 (m, H$_{fur}$, 1H); 4.68 (m, C$_5$H$_4$, 2H); 4.61 (s, CH$_2$, 2H), 4.39 (m, C$_5$H$_4$, 2H); 4.18 (s, C$_5$H$_5$, 5H).

Synthesis of N-ferrocenylidenepyridinylmethanamine (F3)

300 mg (1.4 mmol) of solid ferrocenecarboxaldehyde were introduced in a schlenk. 138 µL (2.1 mmol) of aminomethylpyridine were added. The mixture was dissolved in 20 mL of toluene and the homogeneous mixture was stirred and heated at reflux overnight (16 h). The solution was cooled down to room temperature and the solvent was vaporised under vacuum. After drying overnight under vacuum and at a temperature of 50° C., 379 mg (1.25 mmol) of orange solid were obtained with a yield of 89%.

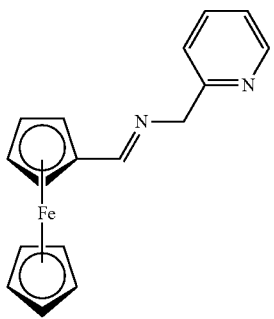

RMN$^1$H (200 MHz, CDCl$_3$): δ 8.58 (m, H$_{pyr}$, 1H); 8.34 (s, CH=N, 1H); 7.68 (m, H$_{pyr}$, 1H); 7.38 (m, H$_{pyr}$, 1H); 7.17 (m, H$_{pyr}$, 1H), 4.80 (s, CH$_2$, 2H); 4.70 (m, C$_5$H$_4$, 2H); 4.40 (m, C$_5$H$_4$, 2H); 4.18 (s, C$_5$H$_5$, 5H).

Oxidation of Ligands.

Synthesis of iodine salt of N-ferrocenylidenebenzylamine (F1+)

374.7 mg (1.28 mmol) of ligand F1 were dissolved in 40 mL of acetonitrile. 325 mg (1.28 mmol) of iodine were added. The homogeneous mixture was stirred at room temperature overnight (16 h). The solvent was vaporised under vacuum and the resulting precipitate was washed three times with 30 mL of diethylether and dried overnight under vacuum. 486.2 mg (1.15 mmol) of dark blue solid were obtained with a yield of 90%. The compound was diamagnetic.

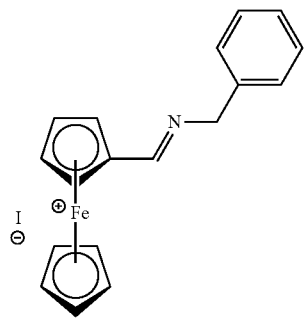

Synthesis of iodine salt of N-ferrocenylidenefurfurylamine (F2+)

381 mg (1.30 mmol) of ligand F2 were dissolved in 40 mL of acetonitrile. 330 mg (1.30 mmol) of iodine were added. The homogeneous mixture was stirred at room temperature overnight (16 h). The solvent was vaporised under vacuum and the resulting precipitate was washed three times with 30 mL of diethylether and dried overnight under vacuum. 507.3 mg (1.20 mmol) of dark blue solid were obtained with a yield of 92%. The compound was diamagnetic.

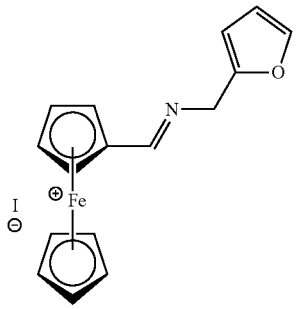

Synthesis of iodine salt of N-ferrocenylidenepyridinylmethanamine (F3+)

379 mg (1.25 mmol) of ligand F3 were dissolved in 40 mL of acetonitrile. 325 mg (1.28 mmol) of iodine were added. The homogeneous mixture was stirred at room temperature overnight (16 h). The solvent was vaporised under vacuum and the resulting precipitate was washed three times with 30 mL of diethylether and dried overnight under vacuum. 459.8 mg (1.06 mmol) of dark solid were obtained with a yield of 85%. The compound was diamagnetic.

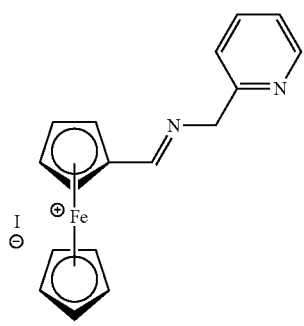

Complexation of Oxidised Ligands with Metallic Precursors

Complexation of oxidised ligand
N-ferrocenylidenebenzylamine (F1+)

With $CrCl_2$ 2.46 mg (20 μmol) of metallic precursor $CrCl_2$ were introduced in a schlenk. 16.9 mg (40 μmol) of oxidised ligand F1+ were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

With $CrCl_3$ 7.49 mg (20 μmol) of metallic precursor $CrCl_3.3THF$ were introduced in a schlenk. 16.9 mg (40 μmol) of oxidised ligand F1+ were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

Complexation of Oxidised Ligand
N-ferrocenylidenefurfurylamine (F2+)

With $CrCl_2$ 2.46 mg (20 μmol) of metallic precursor $CrCl_2$ were introduced in a schlenk. 16.9 mg (40 μmol) of oxidised ligand F2+ were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

With $CrCl_3$ 7.49 mg (20 μmol) of metallic precursor $CrCl_3.3THF$ were introduced in a schlenk. 16.9 mg (40 μmol) of oxidised ligand F2+ were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

Complexation of Oxidised Ligand
N-ferrocenylidenepyridinylmethanamine (F3+)

With $CrCl_2$ 2.46 mg (20 μmol) of metallic precursor $CrCl_2$ were introduced in a schlenk. 17.4 mg (40 μmol) of oxidised ligand F3+ were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

With $CrCl_3$ 7.49 mg (20 μmol) of metallic precursor $CrCl_3.3THF$ were introduced in a schlenk. 16.9 mg (40 μmol) of oxidised ligand F3+ were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

Polymerisation of Ethylene.

The metallic complexes obtained in the previous step were acticated with 1000 equivalents with respect to metal Cr of methylaluminoxane (MAO) 30% in toluene.

The addition of total MAO was carried out in two steps:
1. as activator; and
2. as scavenger, mixed with toluene.

The catalyst component was deposited in a schlenk and 3.25 mL of MAO were added to the schlenk as activating agent (1000 equivalents). The solution was stirred for 5 minutes and then diluted with 1.75 mL of toluene.

The reactor was dried under nitrogen at a temperature of 110° C. for a period of time of 30 minutes. The temperature was raised to 35° C. and 50 mL of toluene were added to the reactor under nitrogen reflux. A solution of scavenger consisting of 1 ml of MAO at 30% and 4 mL of toluene were added to the reactor and the solution was stirred during a few minutes. 20 μmol of the selected catalyst component were added to the reactor under nitrogen reflux. The nitrogen flux was stopped, the reactor was purged and placed under an ethylene pressure of 15 bars. Stirring was continued for a period of time of one hour. The reactor was then purged and the polymerisation was stopped by addition of a 10% solution of MeOH/HCl. The polymer was washed three times with 30 mL of acetone and dried under vacuum overnight at room temperature. The results are displayed in Table 1.

TABLE 1

| Metal salt | Ligand | Activity Kg(PE)/mol(cata)/h | DSC Tm ° C. |
|---|---|---|---|
| $CrCl_2$ | F1+ | 91.6 | 136 |
| $CrCl_3$ | F1+ | 77.5 | 135 |
| $CrCl_2$ | F2+ | 67.2 | 138 |
| $CrCl_3$ | F2+ | 45.2 | 137 |
| $CrCl_2$ | F3+ | 848 | 137 |
| $CrCl_3$ | F3+ | 269 | 135 |

The volume of ethylene cosumed has been studied as a function of time under the following conditions: 5 μmol of catalyst, 1000 equivalents of MAO, ethylene pressure of 15 bars, temperature 35° C., 60 mL of toluene. Overt a period of time of 3 hours, the total amount of ethylene consumed is of 8.51 g amounting to 1703 kg of ethylene per mole of catalyst. The system is selective to the polymerisation of ethylene with no or very little oligomers. The consumption curve is substantially linear during the 3 hours of observation.

The influence of temperature and pressure on the activity have been studied on the complex prepared from 1 equivalent of $CrCl_2$ and 2 equivalents of ligand F3+ (5 μmol of catalyst, 1000 equivalents of MAO, t=1 hour and 60 mL of toluene). The results are displayed in Table 2.

TABLE 2

| T ° C. | Activity kgPE/mol cata/h | | |
|---|---|---|---|
| | P = 15 bars | P = 24 bars | P = 45 bars |
| 25 | 594 (739)* | 1966 (1976) | 2400 |
| 35 | 1200 (1230) | 1800 (1850) | 2600 |
| 55 | 353 | 880 (824) | — |
| 85 | 170 | 714 (674) | — |

It can be concluded that the activity increases with increasing pressure and decreases with increasing temperature with an optimum temperature of 35° C. Decreasing the temperature below 35° C. did not lead to further improvement in activity but indicates the presence of oligomers. Increasing the pressure above 24 bars further improves the activity but the system reaches a plateau in activity after a polymerisation time of 20 to 30 minutes, implying that not enough ethylene is present in the system.

The amount of catalyst was then decreased to 1 μmol instead of the 5 μmol used in the previous example. The conditions were as follows: 1 μmol of catalyst, 1000 equivalents of MAO, p=24 bars, t=1 hour, T=25° C., 60 mL of toluene. After a period of time of 1 hour, 1.6 g of polyethylene were obtained with na activity of 1607 kgPE/mol cata/hour. The ethylene consumption was of 3413 kgC2/mol cata/hour, indicating a consumption larger than the activity. It is postilated that the catalytic system became favourable to the production of oligomers.

Metallic complexes prepared from 1 equivalent of $CrCl_2$ and 1 equivalent of ligand F3+ were not as active as those prepared from 2 equivalent of ligand per equivalent of metallic salt. They had an activity of about 500 kgPE/mol cata/hour, Polymerisation of Propylene.

Propylene has been polymerised with a catalyst component resulting from the complexation of 1 equivalent of $CrCl_2$ with 2 equivalents of ligand F3+. The polymerisation conditions were as follows: 5 μmol of catalyst, 1000 equivalents of MAO, P=5 bars, T=25° C., t=1 hour, 60 mL of toluene. After a reaction time of 1 hour, no polymer was obtained but 1066 kg of propylene were consumed per mole of catalyst per hour resulting in the production of oligomers,

The invention claimed is:

1. A metallic complex obtained by complexation reaction of an oxidised ferricinium ligand of the formula

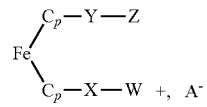

wherein Cp is a cyclopentadienyl group, unsubstituted or substituted, with chelating arms,
wherein X and Y are the same or different with the restriction that at least one Y or X contains at least one chelating group in direct connection with the ferricinium, the other of Y or X being optionally present and wherein X and/or Y are each independently selected to include atoms O, N, P, S or groups —CR=CR—, —CR=N—, —N=CR— or —C≡C— wherein R is H, alkyl or aryl groups having at most 20 carbon atoms,
wherein Z and W are each independently selected from alkyl, aryl, heterocycle group or non-heterocycle group containing ether, thioether, phosphine, imine, amine or amide,
wherein iron has been oxidated with an oxidant capable to oxidate $Fe^{II}$ into $Fe^{III}$ but mild enough to preserve the ligand, and
wherein $A^-$ is an anion associated to $Fe^{III}$
with a metallic precursor $M(Hal)_n R'_{v-n}$ in a solvent, wherein M is a metal Group 6 to 10 of the Periodic Table, each Hal is the same or different and is halogen, each R' is the same or different and is substituted or unsubstituted hydrocarbyl having from 1 to 20 carbon atoms, substituted or unsubstituted aryloxy or alkoxy, v is the valence of M and n is zero or an integer at most equal to v.

2. The metallic complex of claim 1 wherein M is Ni, Co, Cr, Pd or Fe.

3. The metallic complex of claim 2 wherein M is Cr.

4. The metallic complex of claim 1 wherein Hal is chlorine.

5. An active catalyst component comprising the metallic complex of claim 1 and an activating agent having an ionising action.

6. A method for oligomerising or homo- or co-polymerising ethylene and alpha-olefins that comprises the steps of:
   a) injecting the active catalyst system of claim 5 into the reactor;
   b) injecting the monomer and optional comonomer;
   c) maintaining under polymerisation conditions;
   d) retrieving the oligomers and/or polymer.

7. The method of claim 6 wherein the monomer and optional comonomer are each selected from ethylene, propylene or hexane.

* * * * *